United States Patent [19]

Marnay

[11] Patent Number: 5,261,913
[45] Date of Patent: Nov. 16, 1993

[54] DEVICE FOR STRAIGHTENING, SECURING, COMPRESSING AND ELONGATING THE SPINAL COLUMN

[75] Inventor: Thierry Marnay, Clarensac, France

[73] Assignee: J.B.S. Limited Company, Troyes, France

[21] Appl. No.: 935,452

Related U.S. Application Data

[63] Continuation of Ser. No. 671,692, Mar. 26, 1991, filed as PCT/FR90/00539, Jul. 13, 1990, abandoned.

[30] Foreign Application Priority Data

Jul. 26, 1989 [FR] France ................ 89 10178

[51] Int. Cl.$^5$ .............................................. A61F 5/01
[52] U.S. Cl. ..................... 606/61; 403/290
[58] Field of Search ............... 606/53, 60, 61, 62, 606/64, 72, 73; 128/69; 411/378, 388, 389, 396, 397, 401, 411, 366, 374; 439/778, 779; 403/290, 342

[56] References Cited

U.S. PATENT DOCUMENTS

| | | | |
|---|---|---|---|
| 3,019,504 | 2/1962 | Castaglivolo | 403/290 |
| 3,752,203 | 8/1973 | Hill . | |
| 4,011,602 | 5/1977 | Rybicki | 606/72 |
| 4,289,124 | 8/1981 | Zickel | 606/73 |
| 4,411,259 | 10/1983 | Drummond | 606/61 |
| 4,833,342 | 9/1892 | Bolte | 403/290 |
| 4,950,269 | 8/1990 | Gaines, Jr. | 606/61 |
| 5,005,562 | 4/1991 | Cotrel | 606/61 |
| 9,007,717 | 10/1908 | Feaster | 403/290 |

FOREIGN PATENT DOCUMENTS

| | | |
|---|---|---|
| 8707134 | 12/1987 | Australia . |
| 0128058 | 12/1984 | European Pat. Off. . |
| 0242708 | 10/1987 | European Pat. Off. . |
| 3219575 | 12/1983 | Fed. Rep. of Germany . |
| 3639810 | 5/1988 | Fed. Rep. of Germany . |
| 2615095 | 11/1988 | France . |
| 2624720 | 6/1989 | France . |
| 167228 | 9/1921 | United Kingdom . |
| 2173104 | 10/1986 | United Kingdom . |

*Primary Examiner*—Robert A. Hafer
*Assistant Examiner*—David Kenealy
*Attorney, Agent, or Firm*—Pearne, Gordon, McCoy & Granger

[57] ABSTRACT

The invention relates to a process and device for securing, elongating and compressing a spinal column, of simple design, which is easy and precise in use, leaving no projecting part. The process of the invention for straightening and supporting a spinal column consists in securing screwed implants (10) or hooks on either side of the curvature of the spin and interlinking them by at least two rods (20,21) designed to act as struts; said rods (20,21) are introduced longitudinally into grooves (113) perpendicular to the screw (120) fitted in the body (110) of the implants (10) or hooks and then fixed in the base of the grooves (113) by crimping resulting from the deformation of the sides of the groove (113) by the closing of its sides; said deformation is obtained via a conically-threaded nut (30) and a cylindrical male thread cut around the body (110) of the implants (10). Application: straightening and supporting the spinal column in the event of scoliosis or fracture, for example.

14 Claims, 6 Drawing Sheets

DEVICE FOR STRAIGHTENING, SECURING, COMPRESSING AND ELONGATING THE SPINAL COLUMN

This is a continuation of application Ser. No. 07/671,692, filed Mar. 26, 1991, filed as PCT/FR90/00539, Jul. 13, 1990, now abandoned.

The invention concerns a device for straightening and shoring up a spinal column with an abnormal deviation.

Straightening and shoring up a spinal column are two operations that are necessary where there are fractured vertebrae or where there is a deviation of the spinal column as a result of scoliosis or kyphosis, for example.

The known devices for straightening and shoring up spinal columns have been the subject of various embodiments for some years. One of the most well-known is the so-called "Farrington," which is used universally and which we shall describe briefly below, given its relative remoteness from the invention.

The above-mentioned device includes an elongation system and a compression system, located respectively on the concavity and the convexity of the curve of the spinal column; the elongation system basically consists of a cylindrical metal rod on which two braces, a lower one and an upper one, move and can be interlocked so as to be immobile; the lower brace is hooked on the lamina of the lowest vertebra of the curve, and the upper hook is located on the prezygapohysis or highest vertebra of the curve; one end of the rod is notched to allow control of the relative spacing of the two braces and to set the value for that spacing using a locking clamp; the compression system includes a threaded rod on which braces move; their position on the rod can be adjusted by screws that exert pressure on the braces and on the vertebrae.

Such a technique has certain disadvantages basically involving: the lack of precise control over the opening of the curve due to the presence of notches; the fact that support is limited to just the two extreme vertebrae on the curve; the fact that the hooks can turn on the metal rod, since there is no realigningment exerted toward the axis of the trunk nor any partial rotation of the vertebrae from the top; and the fact that there is a risk of the rod breaking.

Most of these disadvantages have been resolved by the creation of devices that use braces on some of the vertebrae on the curve; these elements are composed of a part that forms the brace, a screw or hook, and a body for attaching the shoring-up rod.

There are now three different categories of embodiment of the braces: namely, closed, laterally open and longitudinally open.

Those in the first category require that a rod be placed axially in the brace since the rotating, translating rod is locked in a hole in the brace by means of small screws inserted transversely to the rod.

Now, positioning these rods axially in the body after they have been bent is a very long, exacting operation; it also requires shaking the braces of the braces in which the rod is already inserted, which causes the small pressure screws that clamp said rod to become unscrewed; what is more, these small screws have projecting parts, even when they are broken off at the end of the operation, and can cause wounds and lesions.

Other devices remove some of these disadvantages by providing braces that open laterally; but they still require the use of pressure screws to clamp the rod.

Still other devices have braces with longitudinal openings such as the one described in the following patent:

European Patent 0 128 058, whose object is a spinal shoring and straightening device whose brace has a longitudinal opening; the rod is clamped in the body with supplementary elements, called clamps, composed of small cylindrical-conical rings surmounted by a rectangular body; the whole unit is pierced by a threaded hole designed for screwing in a pressure screw, the element is inserted into the brace, and the pressure screw is screwed in to attach the rod to the brace axially and radially.

These devices are cumbersome in design, considering the large number of parts used; and they do not eliminate projecting parts because there are still screws; these supplementary elements must also be placed on the rod ahead of time and require special orientation of the implants.

Another device which combines the possibility of inserting the rods longitudinally and clamping them with a smaller number of parts was described in the application for the following patent:

French patent application 2 624 720: in which the brace has a longitudinal opening forming a groove, closed by means of a screw cap around the outer portion of the groove; with the final clamping done using a pointed screw inserted into a boss of the cap; this device does not allow for elimination of projecting parts; and the pressure on the rod to clamp it is exerted, on the one hand, only at the contact point of the two opposite edges of the cap and, on the other hand, at the intersection generator and the bottom of the groove, which cannot give perfect clamping, although the clamping in this instance is superior to that of the devices described previously.

This invention is aimed at removing these disadvantages and proposes solving the problem of creating a shoring and straightening device with a simple, inexpensive design that provides for good attachment of the implants on the rods with the shoring function, thus strengthening the solidity of the whole unit, with fast, accurate installation that does not allow any projecting parts to remain.

The spine-straightening and shoring device is composed of threaded implants or hooks connected by at least two rods joined together with braces and connecting elements; said rods are inserted into grooves perpendicular to the screw provided for that purpose in the body of the implants or hooks, then clamped in the bottom of the grooves. It is characterized by the fact that: the rods are clamped in the bottom of grooves made in the body of the implants or hooks that have a deformation effect by joining the sides of the groove by means of a system of cylindrical screws and conical threaded nuts in which the rods are joined to the threaded crosspiece by means of four clamping jaws, one of which is attached to one end of the threaded crosspiece; the positions of the other three on the crosspiece are adjustable by means of a screw in a case, which is rotated by means of an endless wheel and screw system; the screws of the implants are attached by means of a 45° triangular thread, one side of which is located behind the point of the screw and forms a right angle in relation to the rod of the screw; the longitudinal rod-section connecting elements are composed of a milled plate, each end of which has a cylindrical hole for passage of the body of the implant head, which may or may not be separated from its screw, on which a conical threaded nut is mounted. The lateral connecting elements of the rods are composed of a plate with a hole for passage of the body of the head of an implant, which may or may not be separated from its rod, and a groove of the same width which also permits passage of the body of the head of an implant and nuts ensuring that the unit is locked in position; the threaded return rod with two hooks, one facing the other, is mounted in threaded holes with the same pitch that are pierced in the body of said hooks.

The cylindrical screw and conical nut system, which ensures that the sides of the body of the implants or hooks are joined, is composed of a [Dale cylindrical thread around the body of the implants or hooks which are a little shorter in length than the depth of the groove and a threaded conical bore with the same pitch in the axis of the nut; the diameter of the base of the threaded conical bore of the nut corresponds to the diameter of the male cylindrical thread around the body of the implants or hooks; the height of the nut corresponds approximately to the distance separating the entry of the groove of the rod, when the rod is in place in the bottom of said groove.

According to one special embodiment of the invention, the base of the nut includes teeth placed obliquely; the section of said teeth is in the shape of a right triangle whose base merges with that of the nut and whose hypotenuse points in the direction in which the nut is rotated to screw and tighten it.

The teeth which are placed obliquely may be ribbed in circles concentric to the axis of the nut.

According to another embodiment of the invention, the rods serving as stays are threaded all along their length, and the bottom of the groove, made in the body of the implants or hooks, has a semi-cylindrical imprint whose relief corresponds to that of the threads on the shoring rods.

The implants are made of pure titanium or an implantable alloy of titanium, for example, Ti A16 V4.

The endless screw for driving the wheel maneuvering the nut which moves the mobile jaws on the threaded crosspiece has an imprint allowing it to be maneuvered by means of a screwdriver or a wrench.

The means of maneuvering the threaded return rod of the hooks by rotating them two by two can be composed of an imprint allowing it to be maneuvered by means of a screwdriver or a wrench.

The advantages procured by the invention basically consist of the fact that, on one hand, the spinal shoring and straightening device has no projecting parts, once put into place; this is achieved by locking the rod with a roundheaded, conical bore nut, which eliminates the need to use pressure screws; and, on the other hand, by the fact that the locking is done optimally because the pressure exerted to obtain locking is exerted on a large support surface of the rod; this locking is increased by the presence of teeth on the base of the nut that work with the roughness on the rods, or an imprint at the bottom of the groove that works with the threads all along the length of the shoring rod; the device is also simple, fast and accurate in design and use.

Other characteristics and advantages will appear in the following description of several embodiments of the invention given as non-limiting examples, with regard to the figures in the appended plates in which:

FIGS. 11a, 12a, 13a and 14a are top views of it, respectively, and FIG. 13b is a side view of the third embodiment of the hook described.

Figure 1:
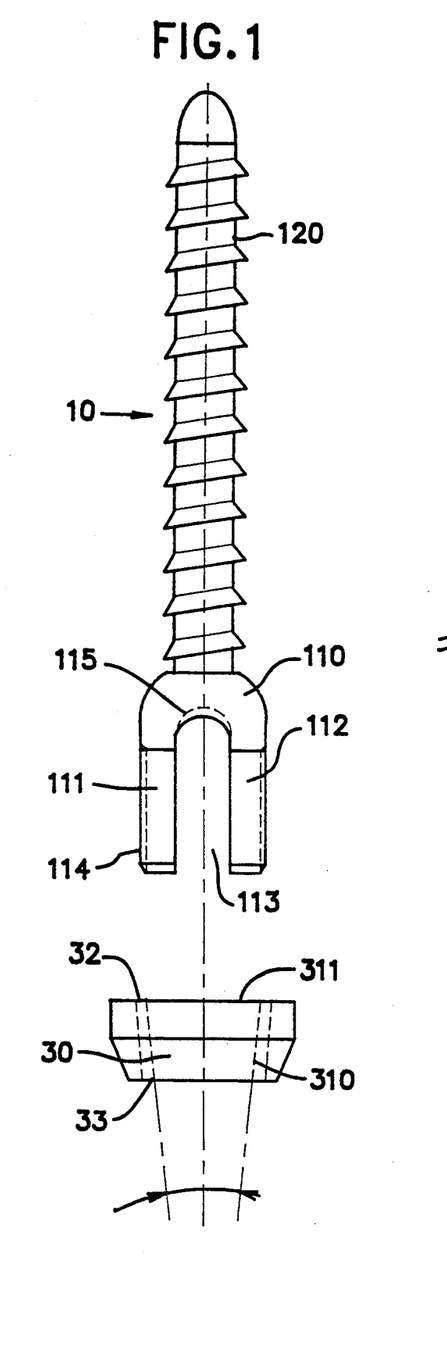
FIG. 1 shows a longitudinal front view of a screw implant and a lateral front view of a nut showing two constituent elements of a special embodiment of the invention.

Referring to FIG. 1, one sees two constituent elements of a special embodiment of the invention, namely an implant 10 and a nut 30; in this embodiment, the implant 10 takes the general form of a screw whose head is formed by a body 110 with a groove 113 made in the plane of the screw 120 of the implant 10, opening into the rear part of the body 110 of the implant 10; and bordered by two parallel sides 111, 112 of said implant 10; there are threads around the body 110, around three quarters of the length of the groove 113 designed to take the threads of the bore 310 of the nut 30.

When the shoring device in the invention is put in place, a shoring rod is inserted on each side of the spinal column successively in the grooves 113 of each implant 10 body 110; the latter are first screwed into the vertebrae located between the two extreme vertebrae of the curve of the spine, or on both sides of a fractured vertebra, depending on the case; then the rod is locked in the bottom of the groove 113 of each implant 10 by the pressure exerted on it; the bottom of each groove 113 is made of a semi-circular part whose diameter corresponds to that of the rod; the pressure is exerted when the nut 30 is screwed around the body 110 of the implant 10, by joining the two sides 111, 112 of the implant 10 bordering the groove 113, one in relation to the other so as to grip the rod and to lock it in the bottom of the groove 113; this can be done by choosing a nut 30 with a conical bore 310, and joining the two sides 111, 112 proportionally to the amount of surface of the bore 310, screwed around the body 110 of the implant 10; the diameter of the base 311 of the bore 310 of the nut 30 corresponds to that of the male cylindrical thread 114 of the implant 10.

Now, whereas the means described above are sufficient to obtain correct locking of the rod in relation to the implant 10, other means have been provided to reinforce this locking, so as to increase the operational safety of the device in the invention; these means are the presence of a semi-cylindrical imprint 115 made in the base of each groove 113, whose relief, as a sort of half-moon thread, is shaped so as to allow it to work with the same relief made all along the length of the shoring rods; thus, positioning the rod in the bottom of the groove 113 will make it possible for the rod to be joined axially in relation to the body 110 of the implant 10 after the nut 30 has been screwed all along its height; pressure will also be exerted on the rod by two opposite edges of the nut 30, on the one hand, and by the sides of the groove 113 on at least half of the periphery of the rod, on the other hand.

It will be noted that the head 33 of the nut 30 has rounded edges and when the nut 30 is in place, its outer side facing the base 32 is located in the plane of the extremity of the sides 111, 112 of the groove 113; in addition, the lateral parts of the nut 30 are in the extension of the non-deformed sides of the body 110 of the implant 10, so that the whole implant 10/nut 30 unit no longer has any projecting parts.

Figure 2:
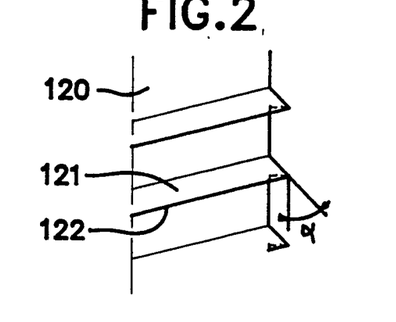
FIG. 2 is a partial representation of the screw showing its triangular thread.

In FIG. 2, it will be noted that the screw 120 connected to the body of the implant has a triangular thread 121 forming a 45° angle; the screw 120 can be self-cutting in some instances of application; it will be noted that one side 122 located in back in relation to the point of the screw 120 forms a right angle in relation to the rod of the implant.

Figure 3:
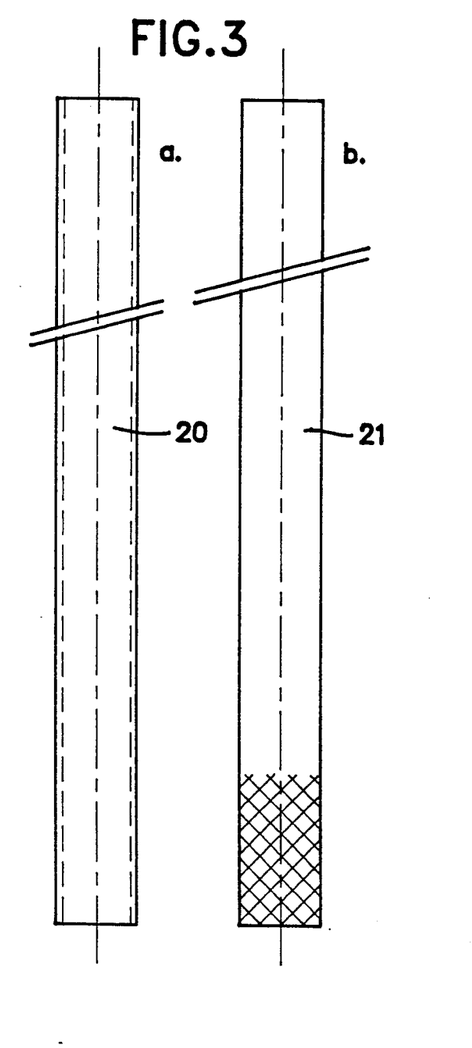
FIG. 3 shows two longitudinal front views of two shoring rods used in two different embodiments of the invention.

In FIG. 3, one can see two shoring rods 20, 21 corresponding to those used in the two different embodiments mentioned above; the first 20 (FIG. 3a) is threaded all along its length, so as to work with the relief in the bottom of the groove of the implants; the second 21 (FIG. 3b) has roughnesses such as those that may result from milling or engine turning, and it can be used in the first embodiment described, although a rod with a smooth surface can also be used here; but this second rod 21 is more especially designed to be used in a third form of embodiment of the device in the invention that will be described below.

Figures 4, 5, 6, 7:
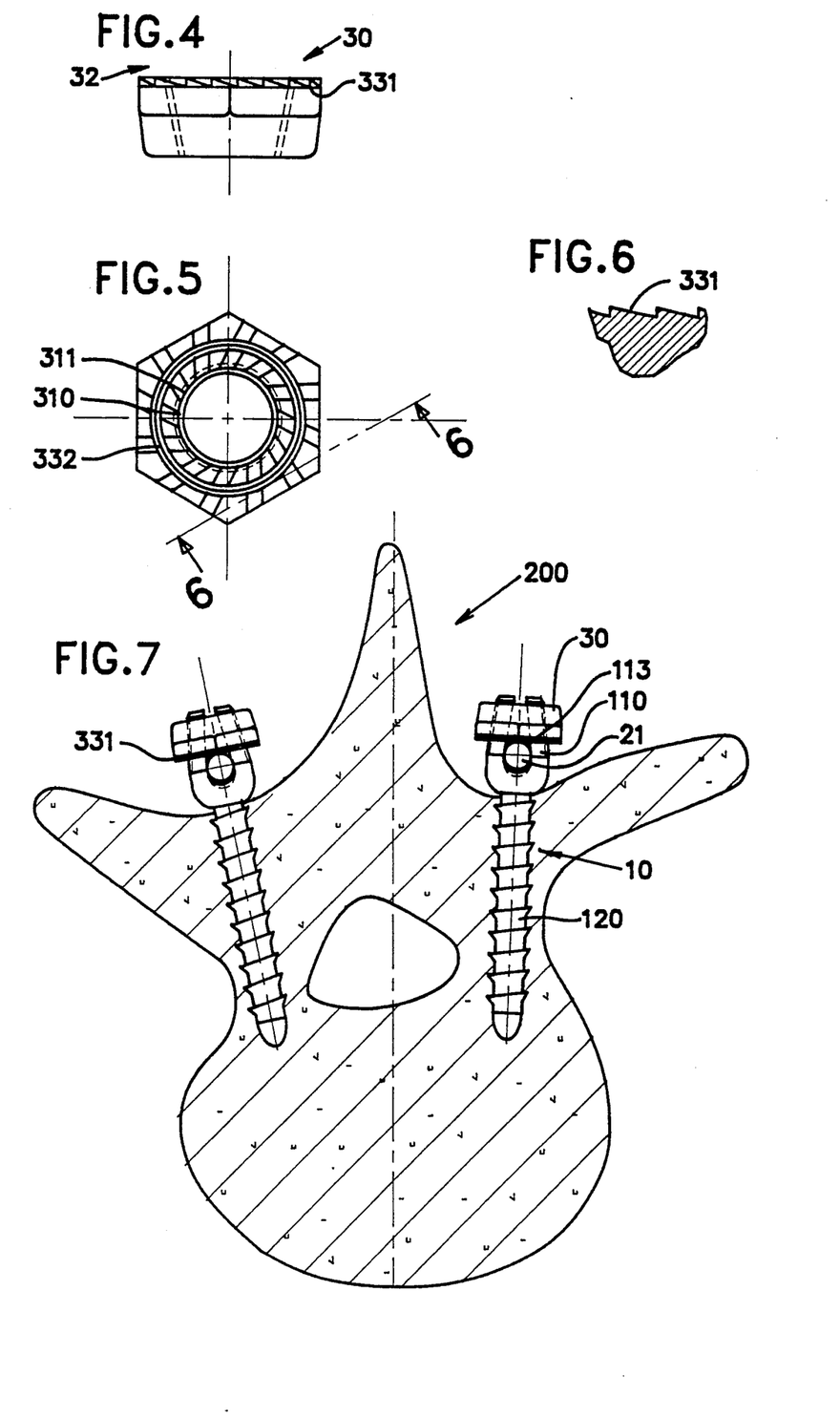
FIG. 4 shows a lateral front view of the nut used in the second embodiment of the invention.
FIG. 5 is a view from below of the same screw corresponding to a third embodiment of the invention.
FIG. 6 is a partial sectional view along A-A of the preceding figure.
FIG. 7 shows a view from above a vertebra with the shoring and straightening device in the invention in position.

In FIGS. 4, 5 and 6, the nut 30 has a series of teeth 331 at its base 32 designed to work with the roughnesses in the surface of the shoring rod, in such a way that the nut 30 moves in relation to the surface of the rod during the final tightening of the nut around the body of the implant, and, on the other hand, so that the rod is locked by inserting the teeth 331 in the holes of the roughness when the nut 30 is involuntarily unscrewed.

These teeth 331 can be placed radially, but in the special embodiment described, they are placed so as to be slightly inclined in relation to the radii of the base 311 of the bore 310 of the nut 30; this peculiarity makes it possible for some teeth 331 always to be engaged in the roughness during unscrewing or in locking position, which is not achieved when the teeth 331 are placed radially; a circular thread 332 has also been provided in order to reinforce the locking of the nut 30.

In FIG. 7, one can see a vertebra 200 into which two implants 10 with screws 120 are screwed; the shoring rod 21 has been put in place in the grooves 113 of the body 110 of the implants 10 and joined to them by a nut 30 screwed around the body 110, whose base has teeth 331, in accordance with the latter embodiment described; this figure lets us consider the supporting surfaces whereby locking pressure is exerted on the rod 21 which are found at the base of the nut 30, on one hand, and at the bottom of the groove 113 on a little more of the semi-periphery of the rod 21, on the other hand.

Figure 8:
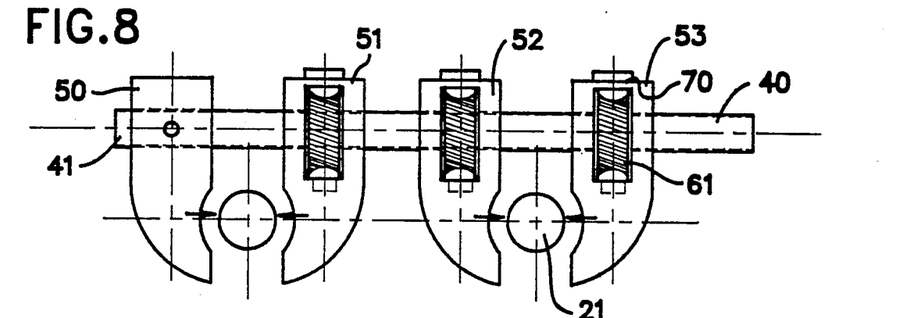
FIG. 8 shows a top view of an embodiment of the connecting device for the two shoring rods, located on either side of a spinal column ensuring its relative tension and spacing.
Figure 9:
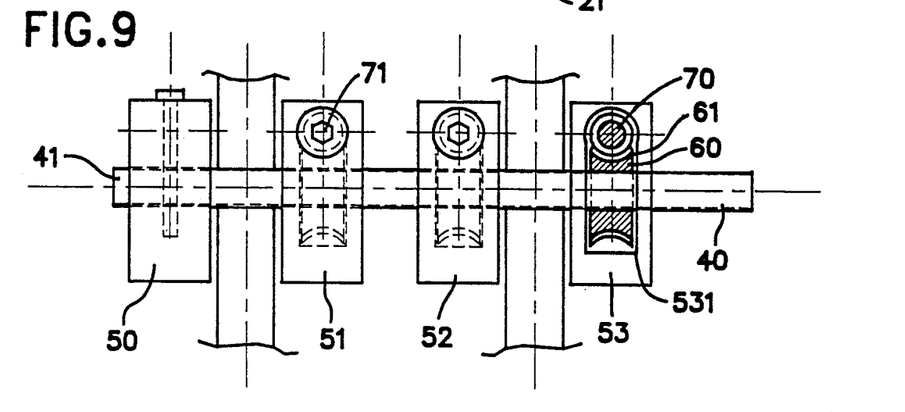
FIG. 9 is a rear view of the same device in section.

Referring to FIGS. 8 and 9, one can see a special embodiment of the device for connecting the two rods 20 and 21 put in place on each side of a spine.

This device is composed of a threaded crosspiece 40, to one end 41 of which has been attached an initial jaw 50 in the general shape of a hook, three other jaws 51, 52, 53 that can move longitudinally on the crosspiece 40 by means of a nut 60 kept in a case 531, joined to the mobile jaw 51, 52, 53 and put into rotation by means of a helicoidal teethed wheel 61 interlocking with the nut 60 and itself placed in rotation by an endless screw 70 whose thread has the same inclination as the teeth of the wheel 61; with the axis of said wheel 61 orthogonal to the axis of the screw 70; with the screw able to be maneuvered manually or automatically because of the presence of a hexagonal imprint 61 by means of an appropriate tool, such as a screwdriver or wrench.

Figure 10:
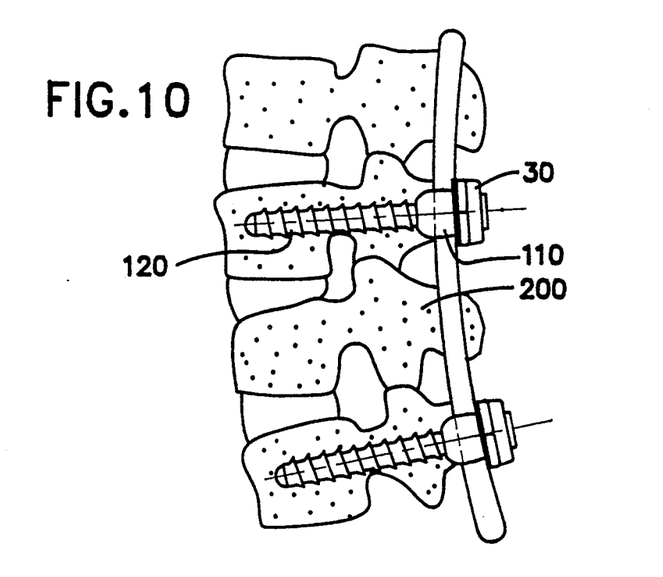
FIG. 10 is a view in a sagittal plane of the shoring device of the invention put into place.
Figure 11:
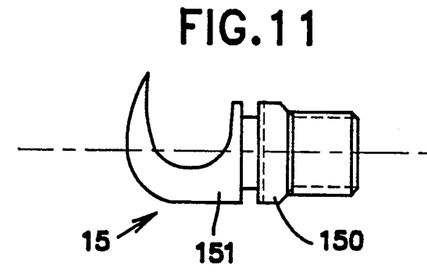
FIGS. 11, 12, 13 and 14 show longitudinal front views of different embodiments of a hook in accordance with the invention.
Figure 12:
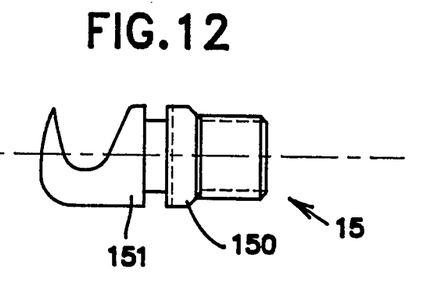
Figure 13:
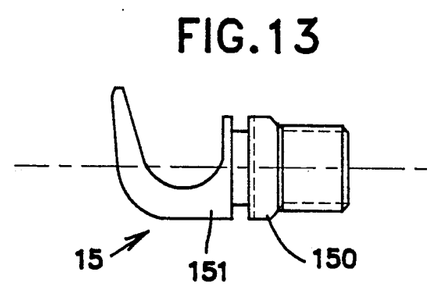
Figure 14:
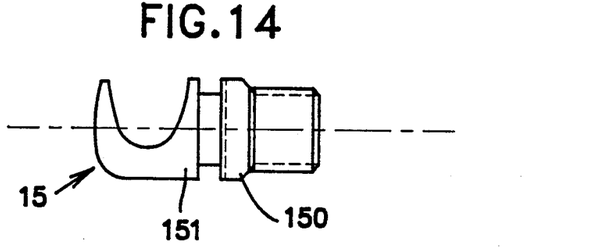

In FIG. 10, it should be noted that the device in the invention, once put into place, has no projecting parts; the screw 120 is screwed into the vertebra 200, with the only projecting parts being the nut 30 and the body of the implant 10.

In FIGS. 11 to 14a, the braces are hooks 15 composed of the hook per se 151 and a body 150 with a groove 152 designed to take a rod like the threaded implants described above.

Figure 15:
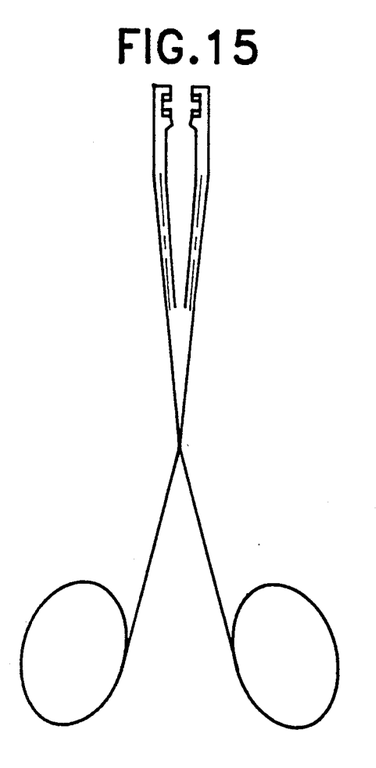
FIG. 15 is a schematic drawing of a pair of pliers used in the invention for handling the hooks.
Figure 16:
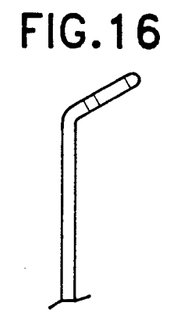
FIG. 16 is a partial side view of the pliers.

The shape of the inside part of the hooks 151 depends on their placement on the vertebrae; their outside part has a lip 153 that is provided to manipulate them with a pair of pliers shown in FIGS. 15 and 16.

Figure 17A:
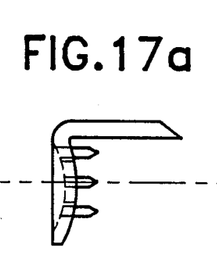
FIGS. 17a, 17b and 17c show three views of a clamp used in the invention.
Figure 17B:
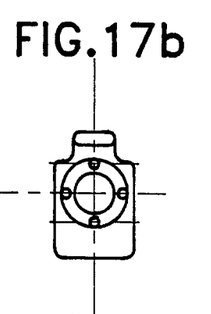
Figure 17C:
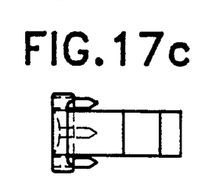

In FIG. 17 (a,b,c), one can see a clamp designed to make it easier to position and maintain the implants in the vertebrae.

Figure 18:
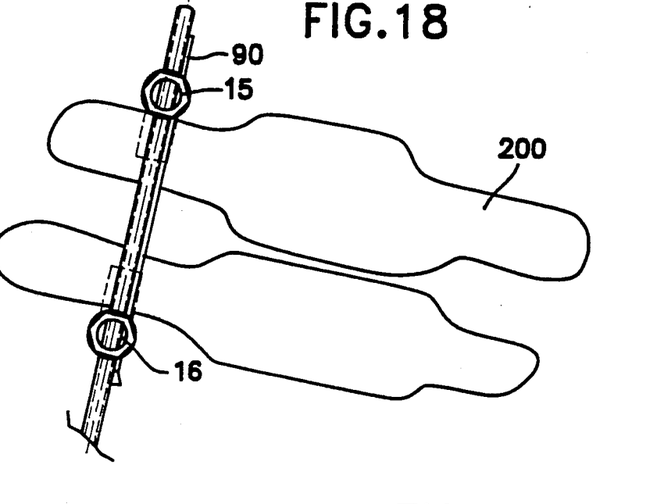
FIG. 18 is a partial view, in a frontal plane, of the device for compression of two vertebrae in accordance with the invention.
Figure 19:
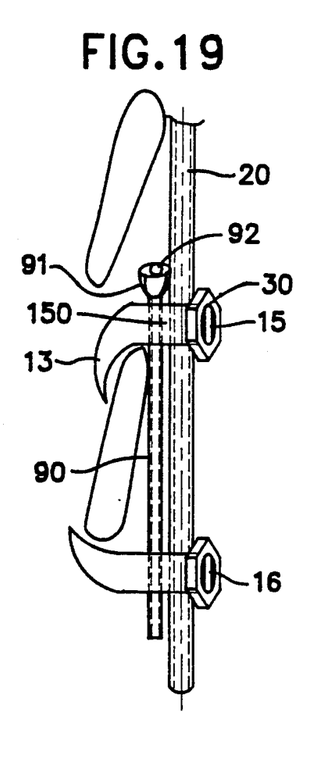
FIG. 19 is a side view of the device for compression of two vertebrae.

In FIGS. 18 and 19, the compression device, for two vertebrae, one in relation to the other, is composed, in a special embodiment, of a threaded rod 90 and two hooks 15, 16 that conform to those of the invention and each of which also has a threaded cylindrical hole with the same pitch as the threaded rod 90; the two hooks 15, 16 are different in length, taking into account the inclined position of the laminae of the vertebrae 200.

In the device's operating position, the body 150 of one of the hooks 16 is stationary, as described above, on the shoring rod 20, while the hook is placed under the lower vertebra and points upward; the other hook 15 is placed on the upper vertebra pointing down and can move along the rod 20 when the threaded rod 90 inserted into the respective holes of the hooks 15, 16 is screwed on with an appropriate tool (not shown), working with an imprint 92 made on the screw head 91, so as to join the two hooks 15, 16 in relation to one another; the hooks 15, 16 on the rod 20 are attached with a nut 30, such as the one described previously.

Such implants can be used for mounting lumbarsacral arthrodesis plates, provided that the upper extremity of the plate has a section of rods with an appropriate diameter allowing it to be attached to the implants attached to the vertebra.

Figure 20:
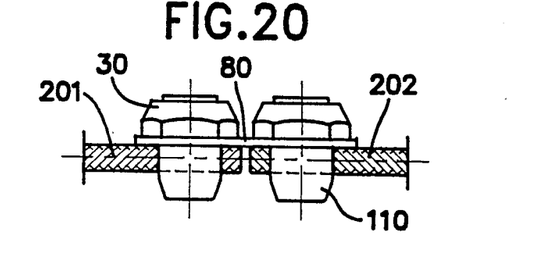
FIG. 20 shows a side view of a device for connecting sections of rods longitudinally.

In FIG. 20, the longitudinal connecting device for the rod sections 201 and 202, according to the invention, is composed of a connecting plate 80 milled on both sides, with two holes whose diameter corresponds to the diameter of the body 110 of the head of the implants 10 which, provided that it is separated ahead of time from its screw 120, can therefore be used as a connecting element for the ends of the rod sections 201 and 202, after they have been inserted into the groove of the body 110 forming the elements and they have been inserted into the holes made in the plate. It is understood that it is then sufficient to lock the unit by means of nuts 30 to achieve effective interlocking of the rods 201 and 202.

Figure 21:
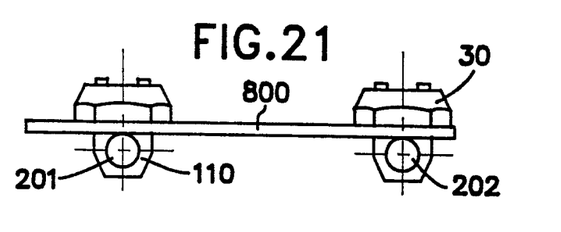
FIG. 21 shows a side view of a lateral rod-connecting device.
Figure 22:
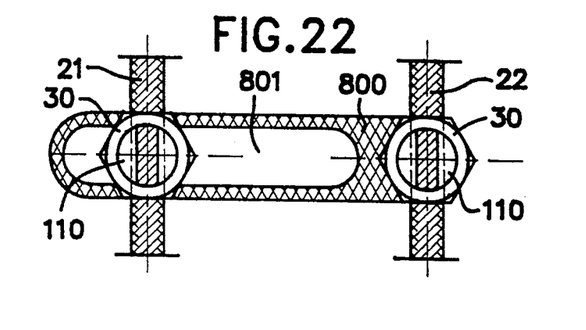
FIG. 22 shows a top view of a lateral rod-connecting device.

In FIGS. 21 and 22, note that the rods 201 and 202 can be easily connected laterally by means of a special milled plate 800, inspired by the one 80 used for longitudinal connection shown in FIG. 20; they differ in that said plate is extended and one hole for passage of the bodies 110 of the implant heads is replaced by a groove 801 with a corresponding width which allows the connection to be adapted to the spacing of the rods required by the position of the implants 10 in the body to which they are attached.

The implants and nuts are made of implantable titanium or titanium alloy; which eliminates problems of allergy or necrosis (the bone loosens around the screw and no longer holds well), which is known with the use of implants made of stainless steel, such as those used in the known devices.

The device is easy and fast to use; indeed, the nuts can be screwed around the bodies of the implants automatically with an appropriate tool.

Positioning precision is increased.

Naturally, the invention is not limited to the embodiment that has just been described and shown. Numerous modifications in detail may be made to it without going beyond the framework of the invention.

I claim:

1. A device for straightening and shoring a spine, comprising:
    spine engaging means including a body having a groove having a bottom and two sides, said groove receiving said spine straightening and shoring rod; and
    a spine straightening and shoring rod;
    a nut having a threaded conical bore and a clamping face, said nut being threadable onto said body thereby clamping said spine straightening and shoring rod between said groove sides by deforming said sides of the groove towards the spine straightening and shoring rod and also clamping said spine straightening and shoring rod between said clamping face and said groove bottom.

2. A device according to claim 1, wherein said spine engaging means further includes a screw projecting from said body.

3. A device according to claim 2, wherein said screw has a thread having one shoulder longitudinally perpendicular to said screw and another shoulder at about 45 degrees.

4. A device according to claim 1, wherein said spine engaging means further includes a hook projecting from said body.

5. A device according to claim 1, wherein little or no portions of the groove sides extend beyond the nut when it is threaded onto the body.

6. A device according to claim 1, wherein said nut has an obliquely grooved face towards the rod and a rounded face opposite to said grooved face.

7. A device according to claim 6, wherein said grooves have a right triangular cross section, the base of the right triangle merging with the face of the nut.

8. A device according to claim 1, wherein said rod is threaded along its length and said bottom of aid groove has a thread-like imprint matching the threads of said rod.

9. A device according to claim 1, wherein said device is made of pure titanium or an implantable alloy thereof.

10. A device according to claim 1, wherein said device is made from Ti A16 V4.

11. A device for straightening and shoring a spine, comprising:
    a plurality of rods;
    a plurality of spine engaging means each including a body having a groove having a bottom and two sides, said groove receiving a selected rod;
    a plurality of nuts having a threaded conical bore, each said nut being threadable onto said body thereby clamping said selected rod between said groove sides by deforming said sides of the groove towards the rod and clamping said selected rod between said nut and said groove bottom; and
    a threaded cross piece for interlocking said rods, said cross piece having a plurality of jaws attached thereto, at least one jaw being movingly attached thereto by a nut caged within said jaw and threaded upon said cross piece, said at least one jaw being movable to clamp said selected rod between two jaws upon rotation of said caged nut.

12. A device according to claim 11, wherein said at least one jaw has an endless screw therein and said caged nut is provided with peripherally threaded means to engage said endless screw, whereby rotation of said endless screw rotates said caged nut thereby moving said at least one jaw along said cross piece, 13. A device for interconnecting spinal column straightening and shoring rods, comprising:
    at least two rod clamping means, each including a body having a groove having a bottom and two sides, said groove receiving one said spinal column straightening and shoring rod;
    linking means having an opening to receive said groove sides of each rod clamping means; and
    at least two nuts, each having a threaded conical bore and a clamping face, said nuts being threadable onto the groove sides of respective rod clamping means thereby clamping respective spinal column straightening and shoring rods between said groove sides by deforming said sides of the groove towards the spinal column straightening and shoring rod and also clamping said linking means and respective spinal column straightening and shoring rods between said clamping face and said groove bottom.

14. A device according to claim 13, wherein said linking means is a milled plate.

* * * * *

UNITED STATES PATENT AND TRADEMARK OFFICE
CERTIFICATE OF CORRECTION

PATENT NO. : 5,261,913

DATED : November 16, 1993

INVENTOR(S) : Thierry Marnay

It is certified that error appears in the above-identified patent and that said Letters Patent is hereby corrected as shown below:

Column 1, line 18, "Farrington" should be --Harrington--.

Column 3, line 14, "[Dale" should be --male--.

Column 7, between lines 47-48, as a separate indent, the phrase "a spine straightening and shoring rod;" should be inserted in between the line ending with "comprising:" and the line beginning with "spine engaging means...".

Column 7, line 52, delete "a spine straightening and shoring rod;".

Column 8, line 14, claim 8, "aid" should be --said--.

Signed and Sealed this

Fourteenth Day of June, 1994

*Attest:*

BRUCE LEHMAN

*Attesting Officer*     *Commissioner of Patents and Trademarks*